US009157129B2

(12) United States Patent
Chaganti et al.

(10) Patent No.: US 9,157,129 B2
(45) Date of Patent: *Oct. 13, 2015

(54) METHODS FOR DETECTING HUMAN PAPILLOMAVIRUS-ASSOCIATED CANCERS

(71) Applicant: Cancer Genetics, Inc., Rutherford, NJ (US)

(72) Inventors: Raju S. K. Chaganti, Hillsdale, NJ (US); Jane Houldsworth, Franklin Lakes, NJ (US)

(73) Assignee: Cancer Genetics, Inc., Rutherford, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/493,803

(22) Filed: Sep. 23, 2014

(65) Prior Publication Data

US 2015/0031017 A1    Jan. 29, 2015

Related U.S. Application Data

(63) Continuation of application No. 13/474,111, filed on May 17, 2012, now Pat. No. 8,883,414, which is a continuation of application No. 13/227,027, filed on Sep. 7, 2011, now Pat. No. 8,865,882.

(60) Provisional application No. 61/380,894, filed on Sep. 8, 2010.

(51) Int. Cl.
*C12Q 1/68* (2006.01)
*C12Q 1/70* (2006.01)

(52) U.S. Cl.
CPC .............. *C12Q 1/708* (2013.01); *C12Q 1/6886* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,919,624 A | 7/1999 | Ried et al. | |
| 7,517,645 B2 | 4/2009 | Sokolova et al. | |
| 8,043,805 B2 | 10/2011 | Sokolova et al. | |
| 8,409,808 B2 | 4/2013 | Ried et al. | |
| 8,603,746 B2 | 12/2013 | Endress et al. | |
| 8,603,747 B2 | 12/2013 | Endress et al. | |
| 2009/0035763 A1 | 2/2009 | Reid et al. | |
| 2012/0164626 A1 | 6/2012 | Sokolova et al. | |

FOREIGN PATENT DOCUMENTS

| WO | WO 2005/001137 A2 | 1/2005 |
|---|---|---|
| WO | WO 2010/011683 A2 | 1/2010 |

OTHER PUBLICATIONS

Arias-Pulido, H., et al., "Mapping common deleted regions on 5p 15 in cervical carcinoma and their occurence in precancerous lesions," *Molecular Cancer*, Oct. 1, 2002, pp. 1-7, vol. 1(3), Open Access.
Atkin, N., "Cytogenetics of Carcinoma of the Cervix Uteri: A Review," *Cancer Genet Cytogenet*, 1997, pp. 33-39, vol. 95, Elsevier.
Caraway, N., et al., "Gain of the 3q26 region in cervicovaginal liquid-based pap preparations is associated with squamous intraepithelial lesions and squamous cell carcinoma," *Gynecologic Oncology*, 2008, vol. 110(1), pp. 37-42.
de Leeuw, R., et al., "Comprehensive whole genome array CGH profiling of mantle cell lymphoma model genomes," *Human Molecular Genetics*, 2004, vol. 13, No. 17, pp. 1827-1837.
Hesselmeyer, K., et al., "Advanced-Stage Cervical Carcinomas Are Defined by a Recurrent Pattern of Chromosomal Abberations Revealing High Genetic Instability and a Consistent Gain of Chromosome Arm 3q," *Genes, Chromosomes & Cancer*, 1997, pp. 223-240, vol. 19, Wiley-Liss, Inc.
Heselmeyer-Haddad, K., et al., "Detection of Genomic Amplification of the Human Telomerase Gene (TERC) in Cytologic Specimens as a Genetic Test for the Diagnosis of Cervical Dysplasia," *American Journal of Pathology*, 2003, vol. 163(4), pp. 1405-1416.
Hopman, A., et al., "Genomic integration of oncogenic HPV and gain of the human telomerase gene TERC at 3q26 are strongly associated events in the progression of uterine cervical dysplasia to invasive cancer," *Journal of Pathology*, 2006, vol. 210(4), pp. 412-419.
Huang, F., et al., "Genetic abnormalities and HPV status in cervical and vulvar squamous cell carcinomas," *Cancer Genetics and Cytogenetics*, 2005, pp. 42-48, vol. 157, Elsevier.
Huang, K., et al., "Chromosomal Gain of 3q and Loss of 11q Often Associated with Nodal Metastasis in Early Stage Cervical Squamous Cell Carcinoma," *J. Formos Med. Assoc.*, 2007, pp. 894-902, vol. 106(11), Elsevier & Formosan Medical Association.
Katz, R., et al., "Automated detection of genetic abnormalities combined with cytology in sputum is a sensitive predictor of lung cancer," *Mod. Pathol.*, 2008, pp. 950-960, vol. 21(8), USCAP, Inc.
Lyng, H., et al., "Intratumor Chromosomal Heterogeneity in Advanced Carcinomas of the Uterine Cervix," *Int. J. Cancer*, 2004, pp. 358-366, vol. 111, Wiley-Liss, Inc.
Macville, M., et al., "Comprehensive and Definitive Molecular Cytogenetic Characterization of HeLa Cells by Spectral Karyotyping," *Cancer Research*, Jan. 1, 1999, pp. 141-150, vol. 59, American Association for Cancer Research.

(Continued)

*Primary Examiner* — Michele K Joike
*Assistant Examiner* — Mindy G Brown
(74) *Attorney, Agent, or Firm* — Alston & Bird LLP

(57) ABSTRACT

The present invention provides probes and methods of use thereof in the diagnosis and/or prognosis of certain types of cancers, particularly human papillomavirus (HPV)-associated cancers. The probes are designed for hybridization with genomic material in a manner indicative of one or more aberrations in the genetic material present in the test sample. The identified aberrations are biomarkers of HPV-associated cancer. The methods of the invention comprise contacting a sample to one or more probes, allowing any genetic material in the sample to hybridize to the genomic regions provided in the probes, analyzing the hybridizations, and analyzing the hybridizations to identify detected aberrations as biomarkers indicative of HPV-associated cancer progression.

21 Claims, 2 Drawing Sheets

(56) References Cited

OTHER PUBLICATIONS

Mertens, F., et al., "Chromosomal Imbalance Maps of Malignant Solid Tumors: A Cytogenetic Survey of 3185 Neoplasms," *Cancer Research*, Jul. 1, 1997, pp. 2765-2780, vol. 57.

Myllykangas, S., et al., "Specificity, selection and significance of gene amplifications in cancer," *Seminars in Cancer Biology*, 2007, vol. 17(1), pp. 42-55.

Olaharski, A., et al., "Tetraploidy and chromosomal instability are early events during cervical carcinogenesis," *Carcinogenesis*, 2006, pp. 337-343, vol. 27(2), Oxford University Press.

Policht, F., et al., "Analysis of genetic copy number changes in cervical disease progression," *BMC Cancer*, 2010, vol. 10(1), p. 432 (twelve pages).

Qin, Y., et al., "Comparative genomic hybridization analysis of genetic aberrations associated with development of esophageal squamous cell carcinoma in Henan, China," *World Journal of Gastroenterology*, Mar. 28, 2008, pp. 1828-1835, vol. 14(12).

Rao, P., et al., "Chromosomal amplifications, 3q gain and deletions of 2q33-q37 are the frequent genetic changes in cervical carcinoma," *BMC Cancer*, 2004, pp. 1-9, vol. 4(5), Open Access.

Seppo, A., et al., "Gain of 3q26: A genetic marker in low-grade squamous intraepithelial lesions (LSIL) of the uterine cervix," *Gynecologic Oncology*, 2009, vol. 114(1), pp. 80-83.

Sokolova, I., et al., The Development of a Multitarget, Culticolor Fluorescence in Situ Hybridization Assay for the Detection of Urothelial Carcinoma in Urine, *Journal of Molecular Diagnostics*, Aug. 2000, pp. 116-123, vol. 2(3), American Society for Investigative Pathology and the Association for Molecular Pathology.

Sokolova, I., et al., "Chromosomal Biomarkers for Detection of Human Papillomavirus Associated Genomic Instability in Epithelial Cells of Cervical Cytology Specimens," *Journal of Molecular Diagnostics*, 2007, vol. 9(5), pp. 604-611.

Tu, Z., et al., "Genomic amplification of the human telomerase Rna gene for differential diagnosis of cervical disorders," *Cancer Genetics and Cytogenetics*, 2009, vol. 191(1), pp. 1016.

Voss, J., et al., "Assessment of Fluorescence in Situ Hybridization and Hybrid Capture 2 Analyses of Cervical Cytology Specimens Diagnosed as Low Grade Squamous Intraepithelial Lesion for the Detection of High Grade Cervical Intraepithelial Neoplasia," *Analytical and Quantitative Cytology and Histology®*, 2010, vol. 32(3), pp. 121-130.

METHODS FOR DETECTING HUMAN PAPILLOMAVIRUS-ASSOCIATED CANCERS

CROSS-REFERENCE TO RELATED APPLICATIONS APPLICATION

This application is a continuation of U.S. application Ser. No. 13/474,111, filed May 17, 2012, which is a continuation of U.S. application Ser. No. 13/227,027, filed Sep. 7, 2011; which claims the benefit of U.S. Provisional Patent Application No. 61/380,894, filed Sep. 8, 2010, which is hereby incorporated herein in its entirety by reference.

FIELD OF THE INVENTION

The present invention provides for the detection of precancers and cancers, particularly those types associated with human papillomavirus (HPV). The diagnostic tool can utilize a probe set for detecting biomarkers in a sample indicative of HPV-associated precancer and cancer. The invention thus also provides methods for the detection of HPV-associated precancer and cancer, preferentially with minimal invasiveness.

BACKGROUND OF THE INVENTION

Papillomaviruses are ubiquitous, small, non-enveloped viruses with a double-stranded DNA genome of about 8 kbp. Papillomaviruses infect squamous basal epithelial cells through wounds or abrasions and encode about 10 proteins involved in viral DNA replication and structure, and in cell transformation (Burd E M., *Clin. Microbiol. Rev.* (2003), 16(1):1-17; and Psyrri A, DiMaio D., *Nat. Clin. Pract. Oncol.* (2008), 5(1):24-31). Duplication of the viral genome absolutely requires host-cell DNA replication components which would otherwise be relatively inactive at this stage of host-cell differentiation but are activated by virally encoded E6 and E7 proteins. The E6 and E7 proteins interact with various host-cell proteins, of which TP53 and RB1, respectively, have been determined to be the functional targets effecting reactivation of cell cycle progression and viral DNA replication. Overall, the process is not cytolytic, with viral DNA evident throughout the thickness of the epithelium and intact virions only apparent in the upper layers.

Infection with HPV is associated with an array of clinical conditions ranging from benign hyperplasias, such as warts and papillomas, to cancer, such as cervical, esophageal, oropharyngeal, vulval, vaginal, penile, and anal types. To date, more than 200 different HPV types have been isolated and are generally categorized into two groups (i.e., low-risk and high-risk) according to the frequency with which they are found in human cancer. Only a small fraction of those individuals infected with high-risk HPV actually develop cancer, which often occurs many years after the initial infection. HPV types 6 and 11 are low-risk types and are generally associated with over 90% of benign lesions. HPV-16 is the most common HPV type found associated with a malignant phenotype and together with HPV-18 exemplifies high-risk HPV types. About 30 HPV types have been identified that are spread through sexual contact and infect primarily the cervix, vagina, penis, and anus (anogenital regions). Of these types, there are four that are mostly found in malignant cells of cervical cancer: HPV-16, HPV-18, HPV31, and HPV-45. Together, HPV-16 and HPV-18 are responsible for 70% of cervical cancer. Worldwide, HPV has been implicated as an etiologic agent in 99.7% of cervical squamous cancer, with evidence that it also plays a role in adenocarcinomas of the cervix.

Many studies over the years, both epidemiologic and molecular in nature, have revealed the causative role of high-risk HPV types in human cancer, mostly with cervical cancer serving as the model system. From a public health viewpoint, once a causative role has been established, the diseases are largely preventable with the use of prophylactic anti-HPV vaccines. For cervical cancer, two such vaccines are available: GARDASIL®, which is directed against HPV types 6, 11, 16, and 18, and CERVARIX®, which is directed against HPV types 16 and 18 (Bosch F X, Castellsague X, de Sanjose S., *Br. J. Cancer* (2008), 98(1):15-21). However, it must be remembered that HPV infection alone is not sufficient for carcinogenesis. Indeed, additional oncogenic events within the host cell must occur in order for malignant transformation to result.

It is estimated that HPV is associated with 500,000 new cases of cervical cancer and 250,000 cervical cancer deaths worldwide each year. Within the US, it was estimated for 2008 that 11,070 new cases would be diagnosed, and about 3,870 women would die of their disease (Jemal A, Siegel R, Ward E, et al., *CA Cancer J. Clin.* (2008), 58(2):71-96). The disease usually presents in several premalignant stages ranging from mild dysplasia (cervical intraepithelial neoplasia grade 1 [CIN1]) to more severe degrees of neoplasia and microinvasive lesions (CIN2 or CIN3), to invasive cancer. Classification of the disease according to this CIN System forms the basis of diagnosis and treatment approaches including therapeutic options and secondary preventive measures. Importantly, CIN1 lesions can regress spontaneously with the risk of progression to severe dysplasia being 1% per year. Risk of progression of moderate dysplastic lesions is 16% within 2 years and 25% within 5 years.

Historically, the primary screening program for this disease has relied upon the cytologic appearance of abnormal cells in the transformation zone of the cervix (Pap test). The results of Pap tests are currently being reported according to the Bethesda classification system (revised in 2001), as outlined in Table 1. The comparable CIN histologic classification is also given.

TABLE 1

Bethesda Classification System for Cervical Squamous Cell Dysplasia

| Bethsesda System | CIN System | Interpretation |
| --- | --- | --- |
| NIL: Negative for intraepithelial lesions or malignancy | Normal | No abnormal cells |
| ASC-US: Atypical squamous cells of undetermined significance | | Squamous cells with abnormalities greater than those attributed to reactive changes |
| ASC-H: Atypical squamous cells, cannot exclude HSIL | | but do not meet the criteria for a squamous intraepithelial lesion |

TABLE 1-continued

Bethesda Classification System for Cervical Squamous Cell Dysplasia

| Bethsesda System | CIN System | Interpretation |
| --- | --- | --- |
| LSIL: Low-grade squamous intraepithelial lesions | CIN 1 | Mildly abnormal squamous cells |
| HSIL: High grade intraepithelial lesions with features suspicious for invasions if suspected | CIN 2/3 | Moderately or severely abnormal squamous cells |
| Carcinoma | Invasive squamous cell carcinoma, invasive glandular cell adenocarcinoma | The possibility of cancer is high enough to warrant immediate evaluation but does not mean that the patient has cancer. |

In the United States, about 55 million Pap smears are performed each year, and of these approximately 5% (2,750,000 smears per year) are diagnosed as containing atypical squamous cells of undetermined significance (ASC-US). It is known that about 39% of women with high grade disease (CIN2/CIN3 or frank cancer) will actually present as ASC-US. Thus, considering the 2,750,000 smears diagnosed as ASC-US each year, just under 10% have underlying CIN3 or cancer. The ASC-US and LSIL Triage Study (ALTS) was established as a NCI-sponsored multicenter randomized trial that would evaluate management options for this group of women including immediate colposcopy (costly), HPV DNA testing for high risk HPV types (less costly, using the Hybrid Capture 2 sold by Qiagen), and repeat cytology examinations (two follow-up visits) ("Human papillomavirus testing for triage of women with cytologic evidence of low-grade squamous intraepithelial lesions: baseline data from a randomized trial. The Atypical Squamous Cells of Undetermined Significance/Low-Grade Squamous Intraepithelial Lesions Triage Study (ALTS) Group. *J. Natl. Cancer Inst.* (2000), 92(5):397-402; and Solomon D, Schiffman M, Tarone R., *J. Natl. Cancer Inst.* (2001), 93(4):293-9). While the ALTS trial indicated that two repeat cytology examinations were as sensitive as HPV DNA testing for detecting CIN3 and cancer (CIN3+) in triaging women diagnosed with ASC-US for follow-up colposcopy, if only one repeat cytologic examination was performed due to cost, then this management option lost sensitivity. Thus, HPV DNA testing is considered an economically viable triaging strategy that should only be used in conjunction with the Pap test. In the study, it reduced the number of patients undergoing colposcopy by 44%. Patients over 21 with ASC-US who are positive for high-risk HPV DNA then, are referred for colposcopy and those who are negative are conservatively managed with repeat Pap smears at 6 and 12 months. In the ALTS trial it was found that of those referred to colposcopy based on a positive HPV test, about 28% actually had CIN2/3+, 23% had CIN1, and the remaining were normal upon biopsy. Clinical management then of this large group with equivocal or mildly abnormal tests every year where follow-up colposcopy is indicated upon a positive HPV test is daunting, and additional triage such as the introduction of the testing of new biomarkers would be desirable.

In patients with LSIL, it was found that 83% had positive HPV DNA tests with little predictive power of regression versus progression. According to the current NCCN Clinical Practice Guidelines in Oncology for Cervical Cancer Screening, women over 21 with ASC, LSIL, or HSIL are currently recommended to undergo colposcopic examination and subsequent treatment according to the biopsy histology. At this stage of patient management, the success of screening heavily depends on the accuracy of the colposcopically-directed biopsies of the approximately 2,000,000 women each year in the US who undergo colposcopy. Subsequent NCI-funded studies are directed both at improving biopsy procedures and the identification of biomarkers to assist in the diagnostic classification of patients who require additional treatment. Patients with normal or CIN1 results may be followed with repeat Pap tests or HPV DNA testing. For those with CIN2/3, further treatment is indicated such as loop electrosurgical excision procedure (LEEP), cryotherapy, cold-knife conization (CKC), or laser ablation. In this case, CIN2 patients are treated as a safety net since biomarkers to identify those lesions that will regress versus progress have as yet to be defined and fully evaluated. Total hysterectomy may be considered for women with CIN3. Diagnosis with invasive carcinoma requires total hysterectomy or external beam high-energy radiotherapy and implants with $^{192}$Ir, depending on the stage. Selected patients also benefit from chemotherapy.

Thus, despite the remarkable successes of cervical cancer screening programs in industrialized countries, improvement in the current screening procedures are warranted to identify women (young and old) with either high-grade disease or low-grade disease with the likelihood of progression, who will require follow-up and treatment for the disease, from those who will be submitted to unnecessary and costly medical procedures. This need arises not only from limitations within current screening tests such as inadequate sampling errors and false-positive and -negative rates, but also due to the inherent nature of the disease, in that as yet few, if any, robust biomarkers to risk-stratify low grade lesions into those likely to regress versus those likely to progress have been identified. Overall then, additional biomarkers of the disease are required, for which assays can be incorporated into screening programs to improve the sensitivity of early cervical cancer detection. From a global health issue, reduction in the costs of any such screening program clearly would positively impact screening coverage of such programs in low resource countries where cervical cancer is prevalent and death rates from the disease are higher.

Another cancer causally associated with HPV is anal cancer, though due to more limited data the exact percent caused by HPV and the most involved types of HPV have yet to be confirmed (Daling J R, Madeleine M M, Johnson L G, et al., *Cancer* (2004), 101(2):270-80). In the U.S. in 2008, 5,070 new cases are estimated to be diagnosed with 680 deaths. So while it is relatively uncommon in the general population, it occurs at a higher rate amongst at-risk populations such as those engaged in receptive anal intercourse. In men who have sex with men (MSM), approximately 40 per 100,000 are affected, with an even higher rate evident in HIV-infected MSM (Chin-Hong P V, Palefsky J M., *Clin. Infect. Dis.* (2002), 35(9):1127-34). Presumably the latter risk factor is due to a compromised immune response and enhanced failure to clear high risk HPV infections. One significant difference between anal HPV in MSM and cervical HPV infection in women is the age at which HPV is prevalent and at which cellular abnormalities are detected (Chin-Hong P V, Vittinghoff E, Cranston R D, et al., *J. Natl. Cancer Inst.* (2005), 97(12):896-905; and Franceschi S, Herrero R, Clifford G M, et al., *Int. J. Cancer* (2006), 119(11):2677-84). Cervical HPV infection is highly prevalent in the few years following initiation of sexual contact, but declines as women enter their 30's and 40's. In contrast, HPV prevalence and cytologic premalignant lesions of the anus in MSM appear to be higher in all adult age groups, an important consideration in the development of a screening program for anal cancer prevention in populations at risk.

As for cervical cancer, classification of premalignant lesions into anal intraepithelial neoplasia grades (AIN1-3) depends on the extent of dysplasia and evidence for neoplasia. The sensitivity for anal cytology for the detection of premalignant and malignant lesions is only around 70% in a high risk population, comparable to that for cervical cancer (Palefsky J M, Holly E A, Hogeboom C J, Berry J M, Jay N, Darragh T M., *J. Acquir. Immune Defic. Syndr. Hum. Retrovirol.* (1997), 14(5):415-22). However, unlike cervical cancer, carcinogenic HPV testing as a screening tool may not be effective for several reasons: high prevalence of high risk HPV in at risk populations, more limited number of HPV types involved, and cross-reactivity of HPV testing with noncarcinogenic HPV types. Thus, for anal cancer in high risk populations, an effective screening program has yet to be defined to guide clinical practice. Currently, clinicians perform anoscopy or high-resolution anoscopy (HRA) as additional workup, which in comparison to colposcopy may only be about 70% sensitive for the detection of premalignant lesions. While there is no consensus that a screening program is warranted for this disease, the introduction of an assay that reduces the number of MSM who undergo the relatively invasive and costly anoscopy procedure will potentially be cost-effective and greatly increase the efficiency with which those whom require immediate treatment are identified.

Over the past 15 years, despite a reduction in the number of people smoking cigarettes, the incidence of head and neck squamous cell cancer (HNSCC) has not declined. The growing subset of HNSCCs associated with HPV are thought to be largely responsible for this. The HPV-associated HNSCCs are commonly oropharyngeal and to a lesser extent pharyngeal in origin. Oropharyngeal cancers form in tissues of the oropharynx, which is the middle part of the throat and includes the soft palate, the base of the tongue, and the tonsils. These cancers seen in a younger non-smoking population are biologically and clinically distinct from carcinogen-induced HNSCC, often associated with sexual behavior, and overall have a better prognosis (Allen C T, Lewis J S, El-Mofty S K, Haughey B H, Nussenbaum B., *Laryngoscope* (2010), 120 (9):1756-72, "Human Papillomaviruses and Cancer: Questions and Answers," National Cancer Institute Fact Sheet, Pub. No. F703, revised Feb. 14, 2008). Early detection screening programs amongst at-risk populations are not in place, and often diagnosis is delayed.

Thus, there is a need for the early detection of HPV-associated precancers and cancers in patients so that appropriate treatment programs can be initiated early in the disease progression. It is an object of the present invention to provide methods for the early detection of HPV-associated precancers and cancers.

BRIEF SUMMARY OF THE INVENTION

The present invention provides methods for identifying an individual with one or more human chromosomal abnormalities diagnostic or indicative of one or more types of HPV-associated precancer and cancer. The methods of the present invention are generally applicable to any one or more types of HPV-associated precancers and cancers including, but not limited to, precancers and cancers of the cervix, anus, vulva, vagina, penis, oropharynx, and pharynx. The methods involve obtaining a sample from an individual, wherein the sample comprises genetic material including, for example, chromosomes. The sample will typically comprise cells from a body tissue or fluid thereof that is expected to comprise the one or more chromosomal abnormalities diagnostic or indicative of one or more types of HPV-associated cancer. Such tissues include, for example, cervical, anal, vulval, vaginal, penile, orophayngeal, and pharyngeal tissues. The methods further involve providing a probe set comprising at least one probe which is individually capable of hybridizing selectively to a specific marker or correlate marker thereof that is associated with a human chromosomal abnormality diagnostic or indicative of one or more types of HPV-associated cancer. The methods further involve using the probe set to determine if the sample comprises at least one of said chromosomal abnormalities. In one embodiment of the invention, fluorescence in situ hybridization (FISH) is used to detect the one or more chromosomal abnormalities.

The present invention further provides methods of identifying in a sample one or more chromosomal abnormalities diagnostic or indicative of one or more types of HPV-associated precancer or cancer. The method comprises providing a probe set comprising at least one probe which is individually capable of hybridizing selectively to a specific marker or correlate marker thereof that is associated with a human chromosomal abnormality diagnostic or indicative of one or more types of HPV-associated cancers. The methods further involve using the probe set to determine if the sample comprises at least one of said chromosomal abnormalities.

Also provided are probe sets for detecting biomarkers in a sample indicative of HPV-associated cancer. The probe sets comprise at least one but preferably two, three or more probes. The probes are individually capable of hybridizing selectively to a specific marker or correlate marker thereof, wherein in said specific marker is associated with a human chromosomal abnormality diagnostic or indicative of one or more types of HPV-associated cancer. Preferably, the one or more probes are selected from the group consisting of a probe that hybridizes to 3q, a probe that hybridizes to 5p, a probe that hybridizes to 20q, and a probe that hybridizes to cen7.

BRIEF DESCRIPTION OF THE FIGURES

Figure 1:
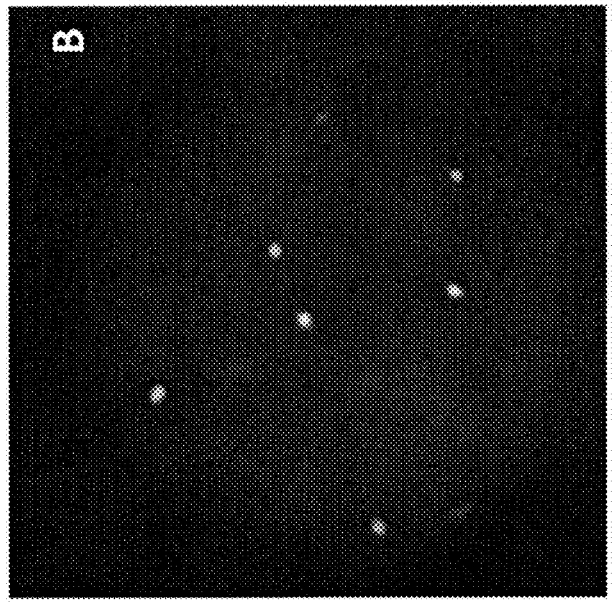
Figure 1:
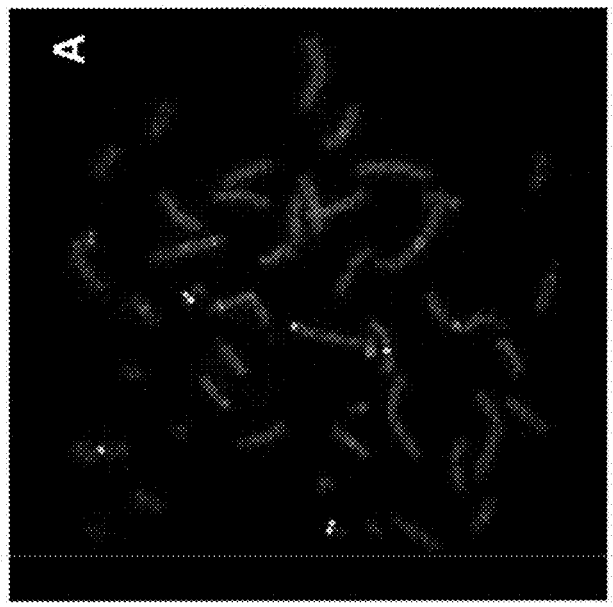
Figure 2:
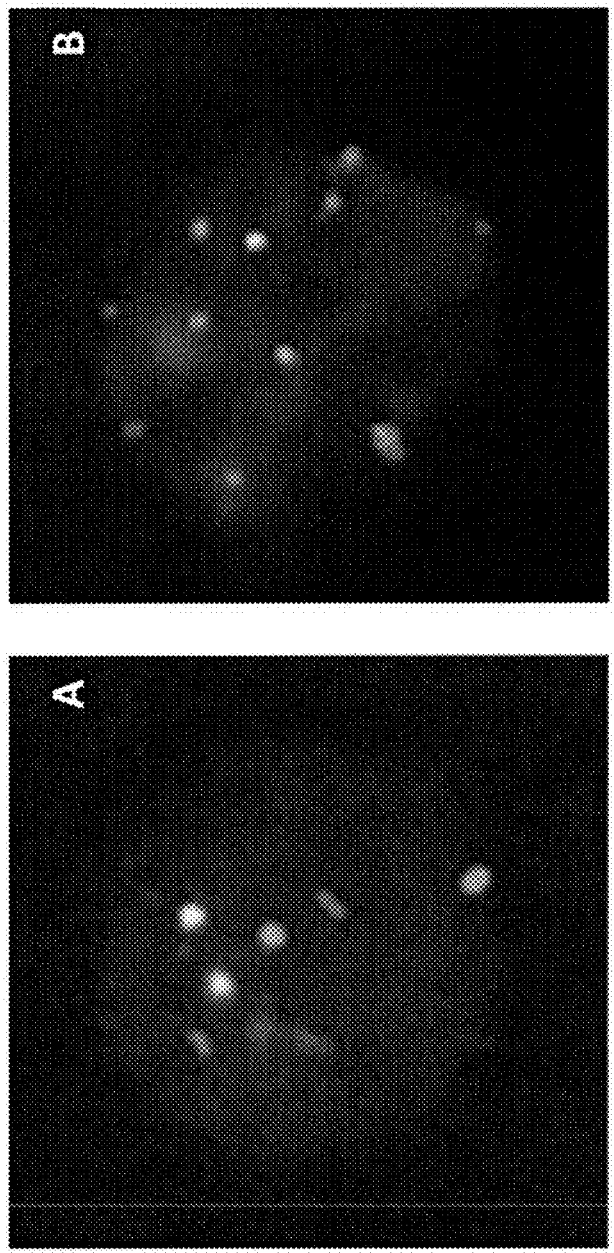

Having thus described the present invention in general terms, reference will now be made to the accompanying drawings, which are not necessarily drawn to scale, and wherein:

FIG. 1 provides representative FISH images of normal lymphocyte metaphase (A) and interphase nuclei (B) showing two each of the 3q (red, R), 5p (green, G), 20q (gold, Go), and cen7 (blue, B) signals (2R, 2G, 2Go, 2B) at the correct chromosomal sites; and FIG. 2 provides representative FISH images of interphase nuclei of liquid-based cervical cytology specimens: normal (A), with a normal hybridization pattern (2R, 2G, 2Go, 2B), and CIN3 specimens (B) with an abnormal pattern (3R, 3G, 3Go, 2B) interpreted as 3q, 5p, and 20q gain.

DETAILED DESCRIPTION OF THE INVENTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Various technical and scientific terms are used in the present disclosure, and the meaning of said terms is understood to be as expressly defined herein or as otherwise ascertainable from the context of the present disclosure. To the extend such terms are not expressly or inherently defined herein, the meaning of such terms is understood to be the same as commonly understood by one of ordinary skill in the art to which this invention belongs.

As used herein, the term "genomic region" is intended to mean a portion of nucleic acid polymer that is contained within the human genome complement. The term also relates to a specific length of DNA contained within bacterial artificial chromosomes (BACs), wherein the DNA has a sequence that corresponds to a portion of the human genome. The term also can be used in relation to specific oligonucleotides that have sequences that correspond to a portion of the human genome. The location of the nucleic acid polymer within the genome can be defined with respect to either the chromosomal band in the human genome or one or more specific nucleotide positions in the human genome.

As used herein, the terms "cancer" and "cancerous" are intended to mean the physiological condition in mammals that is typically characterized by unregulated cell growth. Examples of cancer include any cancer associated with HPV, including, for example, cancers of the cervix, anus, vulva, vagina, penis, oropharynx, and pharynx.

As used herein, the terms "precancer" and "precancerous" are intended to mean the physiological condition in mammals that is typically characterized by unregulated cell growth that will progress to cancer. Examples of precancer include any precancer associated with HPV including, for example, precancers of the cervix, anus, vulva, vagina, penis, oropharynx, and pharynx.

As used herein, the terms "biopsy" and "biopsy specimen" are intended to mean a biological sample of tissue, cells, or liquid taken from the human body.

As used herein, the term "genetic material" is intended to mean materials comprising or formed predominately of nucleic acids. The term specifically is intended to encompass, deoxyribonucleic acids (DNA) or fragments thereof and ribonucleic acids (RNA) or fragments thereof. The term also can be used in reference to genes, chromosomes, and/or oligonucleotides and can encompass any portion of the nuclear genome and/or the mitochondrial genome of the human body.

As used herein, "gain" of a chromosomal segment (e.g., "gain of 3q" or "3q gain") refers to multiplication (amplification) of all or any part thereof of the chromosome segment resulting in increased copy number of the segment. In one embodiment of the invention, "gain of 3q" is multiplication (amplification) within 3q26.

As used herein, "loss" of a chromosomal segment (e.g., "loss of 3q" or "3q loss") refers to a deletion of all or any part thereof of the chromosome segment resulting in decreased copy number of the segment.

As used herein, "tetraploidy" refers to a duplication of the chromosomal complement as occurs during the normal process of cell division.

As used herein, the term "label" is intended to mean any substance that can be attached to a probe so that when the probe binds to a corresponding site a signal is emitted or the labeled probe can be detected by a human observer or an analytical instrument. Labels envisioned by the present invention can include any labels that emit a signal and allow for identification of a component in a sample. Non-limiting examples of labels encompassed by the present invention include fluorescent moieties, radioactive moieties, chromogenic moieties, and enzymatic moieties.

As used herein, the term "probe" is intended to mean any molecular structure or substructure that hybridizes or otherwise binds to a genomic region.

As used herein, a "marker", "cellular marker", "biomarker", molecular marker", or "disease marker" is any molecular structure or substructure that is correlated with a disease state or pathogen. Broadly defined, a marker is a biological indicator that may be deliberately used by an observer or instrument to reveal, detect, or measure the presence or frequency and/or amount of a specific condition, event or substance. For example, molecular markers are specific molecules, such as proteins or protein fragments, whose presence within a cell or tissue indicates a particular disease state.

As used herein, "cytogenetic abnormality" when used in singular or plural, shall mean an alteration in the human genome that can be detected by examination of the chromosomes. A "cytogenetic abnormality" is also referred to herein as a "chromosomal abnormality".

As used herein, "cytogenetic assay" shall mean a laboratory assay that examines chromosomes.

As used herein, "BAC" (Bacterial artificial chromosome) is a laboratory creation involving an artificially constructed chromosome in which medium-sized segments of DNA (100,000 to 300,000 bases in length) that come from another species are cloned into bacteria. Once the foreign DNA has been cloned into the bacteria's chromosome, many copies of it can be made (amplified) and sequenced. Bacterial artificial chromosome is abbreviated BAC.

Many studies over the years, both epidemiologic and molecular in nature, have revealed the causative role of high-risk human papillomavirus (HPV) types in human cancer, particularly those of the anogenital region, including, but not limited to, cervical and anal cancers. The etiologic course of such HPV-associated cancers has been suggested to involve infection by HPV, persistence of the infection, progression to an immediate precursor of cancer, and finally invasion (the latter two steps requiring additional host oncogenic events). Successful screening programs based on the appearance of abnormal cells in cytology specimens, and more recently HPV-type, have been implemented for cervical cancer; however, there is a great need to identify additional biomarkers to increase the sensitivity with which precancer and cancer are detected in cytology specimens. The present invention achieves this end and can provide additional triage of the approximately 2,000,000 women each year in the U.S. who undergo colposcopy for follow-up of abnormal cytology, reducing the performance of costly and often unnecessary procedures, and ultimately increasing the cost-effectiveness of the overall screening program leading to increased global population coverage by such programs.

The present invention is not limited to methods for identifying an individual that has HPV-associated precancer and cancer of the cervix and anus. The methods of the present invention are generally applicable to any one or more types of HPV-associated precancers and cancers including, but not limited to, precancers and cancers of the cervix, anus, vulva, vagina, penis, oropharynx, and pharynx.

Gain of 3q and to a lesser extent gain of 5p and 20q, are genomic abnormalities commonly detected in HPV-associated cancers, and as such represent potential biomarkers of HPV-associated cancer progression. The present invention is, in certain embodiments, a fluorescence in situ hybridization (FISH)-based HPV-associated cancer detection test (FHACT) to detect genomic abnormalities in cervical, anal, vulval, vaginal, penile, oropharyngeal, and pharyngeal specimens. In further embodiments, the invention can provide for use of the test in HPV-associated cancer screening programs.

In specific embodiments, the invention provides a robust, sensitive, and specific FISH-based test that, together with standard cytology and HPV-typing, can provide for accurate detection of precancer and cancer in cytology specimens. Such test can significantly impact standard-of-care recommendations in HPV-associated cancer screening programs and can identify patients requiring additional follow-up and treatment.

The present invention provides for the assessment of genomic alterations in the diagnosis and prognosis of precancer, particularly HPV-associated cancer. In particular, the invention provides the ability to use hybridization technology, such as fluorescence in situ hybridization (FISH), as a clinical tool for the diagnosis and prognosis of HPV-associated cancer.

In one aspect, the invention can provide a probe set for detecting biomarkers in a sample that are indicative of HPV-associated cancer. In certain embodiments, the probe set can comprise a plurality of labeled, distinct genomic regions, such as DNA fragments (including bacterial artificial chromosomes [BACs]). Preferably, each of the distinct genomic regions is individually capable of hybridizing to material present in the sample. Moreover, the genomic regions in the probe set can be regions wherein an alteration therein is correlated to one or more types of HPV-associated cancer (i.e., are biomarkers indicative of HPV-associated cancer progression).

In another aspect, the invention also can provide methods of detecting biomarkers in a sample indicative of HPV-associated cancer progression. Such methods can be useful to identify precancer cells, formations, or the like, as well as early and/or late stage cancer. In certain embodiments, a method according to the invention can comprise the following steps: (a) providing a probe set as described herein; (b) providing the sample with genetic material therein; (c) hybridizing the genetic material in the sample with the probe set; (d) analyzing the hybridization pattern of the genetic material in the sample to the probe set to detect patterns indicating the presence of alterations in the genetic material from the sample; and (e) identifying any detected alterations as biomarkers indicative of HPV-associated cancer progression. In specific embodiments, the method of the invention particularly comprises fluorescence in situ hybridization (FISH).

In order to improve the clinical utility of cervical/anal cytology and HPV testing in cancer prevention screening programs, there is great interest to identify additional biomarkers of progression from HPV-infected tissue to dysplasia, and then to neoplasia. In the former case, it is the altered expression of the viral oncogenes E6 and E7 that deregulate host cell cycle control, effectively leading to unregulated cell proliferation associated with chromosome instability. Such chromosome instability is manifested as numeric and structural chromosomal abnormalities, and as such provides the viral genome with multiple sites at which stable integration into the host genome is possible. For each of these molecular events, both direct and surrogate biomarkers have been studied to varying extents, with often small study cohorts, and with varying success of translation into possible screening tools, as reviewed recently by Wentzensen and Doeberitz (Dis. Markers (2007), 23(4):315-30). Of particular note, levels of expression of $p16^{INK4a}$ by immunohistochemical methods in both lesions and exfoliated cells has performed well within an ASCUS/LSIL triage study and additional studies are planned to evaluate biochemical methodologies for $p16^{INK4a}$ expression analysis for translation into a technically feasible screening tool.

As for most cancers, cervical cancers exhibit a variety of nonrandom chromosomal abnormalities, and DNA aberrations as revealed by conventional karyotype analysis, molecular cytogenetic analyses (FISH, chromosomal comparative genomic hybridization [CGH], and array-CGH), and a variety of molecular biologic analyses, each with their own set of limitations. Conventional karyotype analysis of cervical cancer specimens has indicated the nonrandom involvement of structural abnormalities of chromosomes 1, 3, 5, 11, and 17, primarily as deletions of the short arms, except for chromosome 5 where an isochromosome of the short arm is evident (resulting in an overall gain of 5p) (Atkin N B., Cancer Genet. Cytogenet. (1997), 95(1):33-9). Application of CGH and more recently array-CGH to cervical cancer specimens by several groups have delineated commonly gained and deleted regions though with the frequency of the gain/lost varies markedly between the studies (Table 2) (Allen D G, White D J, Hutchins A M, et al., Br. J. Cancer (2000), 83(12):1659-63; Heselmeyer K, Schrock E, du Manoir S, et al., Proc. Natl. Acad. Sci. U.S.A. (1996), 93(1):479-84; Kirchhoff M, Rose H, Petersen B L, et al., Genes Chromosomes Cancer (1999), 24(2):144-50; Lyng H, Beigi M, Svendsrud D H, et al., Int. J. Cancer (2004), 111(3):358-66; Ng G, Winder D, Muralidhar B, et al., J. Pathol. (2007), 212(3):325-34; BMC Cancer (2004); 4:5; Scotto L, Narayan G, Nandula S V, et al., Genes Chromosomes Cancer (2008); Scotto L, Narayan G, Nandula S V, et al., Mol. Cancer (2008), 7:58; Umayahara K, Numa F, Suchiro Y, et al., Genes Chromosomes Cancer (2002), 33(1):98-102; Alazawi W, Pett M, Strauss S, et al., Br. J. Cancer (2004), 91(12):2063-70). In Table 2, alterations are those found in at least two independent CGH and/or array-CGH studies of cervical cancer. Respective data for premalignant lesions were then listed. Areas where no study was conducted are denoted with the symbol "-".

TABLE 2

Summary of Genomic Copy Number Alterations in Cervical Cancer Specimens Detected by CGH and/or Array-CGH*

| Chromosome | Change | ASC-US | LSIL (CIN1) | HSIL (CIN2/3) | Cancer |
|---|---|---|---|---|---|
| 1p | Gain | — | 0-79% | 18-80% | 27-45% |
| 1q | Gain | — | 0% | 18-21% | 20-50% |
| 2q | Loss | — | 13-26% | 18-33% | 31-57% |
| 3p | Loss | — | 0% | 3-8% | 20-56% |
| 3q | Gain | — | 0-6% | 8-48% | 40-90% |
| 4p | Loss | — | 19% | 18-21% | 25-40% |
| 4q | Loss | — | 13-47% | 12-53% | 20-36% |
| 5p | Gain | — | — | — | 30-58% |
| 6q | Gain | — | 26% | 18-43% | 20-38% |
| 8q | Gain | — | — | 18% | 25-41% |
| 9q | Gain | — | 47% | 12-45% | 20-25% |
| 10q | Loss | — | — | — | 16-31% |
| 11q | Loss | — | 19% | 12-27% | 25-67% |
| 13q | Loss | — | 21% | 18-25% | 20-43% |
| 17p | Loss | — | 0% | 0% | 25-30% |
| 19p | Gain | — | — | — | 17-35% |
| 20p | Gain | — | — | — | 18-45% |

TABLE 2-continued

Summary of Genomic Copy Number Alterations in Cervical
Cancer Specimens Detected by CGH and/or Array-CGH*

| Chromosome | Change | ASC-US | LSIL (CIN1) | HSIL (CIN2/3) | Cancer |
|---|---|---|---|---|---|
| 20q | Gain | — | 32% | 12-47% | 26-65% |
| Xq | Gain | — | — | — | 17-34% |

For several regions, minimal regions could be identified (e.g., 3q26 and 8q24), but not for others (e.g., 5p), and for 3q26, the candidate target gene of the gain/amplification is thought to be the gene encoding the RNA component of telomerase (TERC) (Sugita M, Tanaka N, Davidson S, et al., *Cancer Genet. Cytogenet.* (2000), 117(1):9-18). Follow-up FISH analyses were performed in several studies to confirm the locus gain/loss using appropriately mapped probes (Caraway N P, Khanna A, Dawlett M, et al., *Gynecol. Oncol.* (2008), 110(1):37-42; Heselmeyer-Haddad K, Janz V, Castle P E, et al., *Am. J. Pathol.* (2003), 163(4):1405-16; and Hopman A H, Theelen W, Hommelberg P P, et al., *J. Pathol.* (2006), 210(4):412-9). Importantly, it is gain of 3q, 5p, and 20q that comprise genetic lesions homogenously detected in multiple biopsies of individual tumors. Even fewer studies have identified regions of the genome that are gained/lost in premalignant lesions indicative of their possible roles early in development of the disease (Table 2). Comparable CGH and array-CGH studies for other HPV-associated cancers have been performed and while the studies are much fewer in number, it is clearly apparent that some chromosomal abnormalities are shared between these diseases. For anogenital HPV-associated cancers, these include gain of 1p, 1q, 3q, and 20q and loss of 2q, 4p, 11q, and 13q in anal cancer and premalignant AIN lesions, and gain of 1q, 3q, 5p, 6q, and 19p in vaginal cancer (Gagne S E, Jensen R, Polvi A, et al., *J. Acquir. Immune Defic. Syndr.* (2005), 40(2):182-9; Habermann J K, Hellman K, Freitag S, et al., *Cancer Genet. Cytogenet.* (2004), 148(1):7-13; Haga T, Kim S H, Jensen R H, Darragh T, Palefsky J M., *J. Acquir. Immune Defic. Syndr.* (2001), 26(3):256-62; Heselmeyer K, du Manoir S, Blegen H, et al., *Br. J. Cancer* (1997), 76(10):1271-8; Palefsky J., *Adv. Dent. Res.* (2006), 19(1):99-105).

Since FISH is a more sensitive and robust molecular cytogenetic technique than CGH, several groups have initiated studies to determine at which stage in the disease, the common genomic abnormalities are detected. To date, the gain of 3q, 5p, and 20q have been assayed (Table 3), being the most commonly and consistently observed genomic copy number alterations in cervical cancer, which are also found in the other anogenital cancers (Mian C, Bancher D, Kohlberger P, et al., *Gynecol. Oncol.* (1999), 75(1):41-6). Again it is apparent that great variability occurs in the reported frequencies, which can be mostly accounted by the use of differing cut-offs for the presence/absence of the abnormality. Of note, Heselmeyer-Haddad et al. also developed algorithms to permit classification of HSIL specimens, that were dependent on the cut-off used. Overall though, there is evidence that these abnormalities are present in precancerous lesions and may have roles in cervical carcinogenesis. Indeed, in a follow-up study by Heselmeyer-Haddad et al. (*Am. J. Pathol.* (2005), 166(4):1229-38) of precancerous used pap smears (total of 59), gain of 3q (TERC) was associated with progression of CIN1/CIN2 lesions to more dysplastic lesions, while none of the CIN1/CIN2 cases that regressed showed the abnormality, using cut-offs re-established for used cervical smears. The sensitivity of prediction of progression was 100% and specificity was 70%. Additionally, gain of 3q was found in 33% of cytologically normal smears from women who at later times displayed CIN3 or cervical cancer. Thus, at least for gain of 3q, there is preliminary evidence that this genomic lesion may serve as biomarker of disease progression.

TABLE 3

FISH Analysis of Gain of 3q, 5p, and 20q in Premalignant and Malignant Cervical Cancer Specimens

| Study | Specimen Type | Region | ASC-US | LSIL (CIN1) | HSIL (CIN2/3) | Cancer |
|---|---|---|---|---|---|---|
| Mian et al, 1999 (33) | 22 cervical smears | 3 | — | 20% | 41% | — |
| Heselmeyer-Haddad et al, 2003 (26) | 57 thin-layer slides | 3q26 (TERC) | 0% | 7% | 92% | — |
| Hopman et al, 2006 (27) | 30 paraffin sections | 3q26 (TERC) | — | — | 18% | 54% |
| Caraway et al, 2008 (25) | 66 liquid-based specimens | 3q26 (TERC) | 13% | 70% | 100% | 100% |
| Scotto et al, 2008 (21) | 144 frozen/paraffin sections/cervical smears | 5p | 0% | 0% | 26% | 63% |
| Scotto et al, 2008 (20) | | 20q | 0% | 21% | 28% | 55% |

As mentioned above, it is HPV infection that is thought to lead to chromosomal instability (resulting in the abnormalities described above) and ultimately transformation. To this end, associations between HPV infection and particular genomic abnormalities have been assessed. A recent FISH study combined detection of the HPV genome with the detection of 3q and 8q gain in 235 residual liquid cervical specimens (Sokolova I, Algeciras-Schimnich A, Song M, et al., *J. Mol. Diagn.* (2007), 9(5):604-11). This study showed an increase in the number of "double positive" cells (positive for both HPV and 3q and/or 8q gain) with increasing degree of dysplasia and using a cut-off of four cells, that 80% of CIN2/3 cases were "double positive". A previous study indicated that integration of the HPV genome into the host genome was associated with 3q26 (TERC) gain.

Overall then, there exist genomic abnormalities (gain of 3q, 5p, and 20q) that are shared to some extent in several HPV-associated diseases, and for which there is some preliminary evidence suggesting an early role in carcinogenesis.

In interphase FISH, a single-stranded fluorescent-labeled nucleic acid sequence (probe) complementary to a target genomic sequence is hybridized to metaphase chromosomes and interphase nuclei to detect the presence or absence of a given abnormality (Patel A S, Hawkins A L, Griffin C A, *Curr. Opin. Oncol.* (2000), 12(1):62-7; and Carpenter N J, *Semin. Pediatr. Neurol.* (2001), 8(3):135-46). The chief advantage of FISH is that it can be applied to non-dividing (interphase) cells and a variety of specimen types. Depending on the color scheme and placement of the probes (spanning or flanking the genomic region of interest), interpretation of hybridized nuclei preparations can involve counting of hybridization signals per nucleus (genomic gain/loss), identification of fusion hybridization signals (rearrangement), or identification of signals that break apart (rearrangement). For the most part, in a clinical laboratory setting, FISH is considered an adjunct to traditional G-banding metaphase chromosome analysis. Even in this capacity, the impact of FISH-based assays on patient management is well established for a broad range of cancers for both diagnostic and prognostic purposes. To date, two FISH-based tests have been FDA-approved in cancer: PATHVYSION® (Abbott Molecular, Inc./Vysis, Inc.) for the detection of HER2 amplification in breast cancer to assist in treatment decisions, and UROVYSION™ (Abbott/Vysis) for the detection of aneuploidy associated with bladder cancer in urine specimens. In these tests, a FISH-based assay is being utilized in clinical management of patients in conjunction with morphologic examination (pathology and cytology respectively) and not metaphase chromosome analysis. In addition, both assays involve enumeration of signals per nucleus (cut-offs established by the manufacturer based on large cohort studies), which lends itself for automation using systems such as the Metafer (MetaSystems). Such systems are currently in routine use in clinical laboratories for assays such as UROVYSION™. Thus, commercial precedence exists for the use of highly sensitive FISH-based assays in diagnostic and prognostic clinical settings in solid tumors.

While HPV infection plays a major role in the development of cervical and anal cancer, additional host oncogenic events are involved. Molecular cytogenetic and genetic studies have identified a number of genomic abnormalities that are shared between these cancer types that potentially harbor oncogenes or tumor suppressor genes. For several of these regions, candidate genes have been suggested though none have experimentally been confirmed to have such a role. Despite this, these abnormalities serve as biomarkers of HPV-associated cancers, but it is unknown at which stage in the etiology of these cancers, these abnormalities are observed. HPV-associated cancers are thought to follow a course from initial infection, to persistence of the infection, to progression into a precancerous lesion that ultimately becomes invasive cancer. For cervical cancer, there is reasonable evidence to suggest that gain of 3q is a genomic alteration that is associated with progression of the disease into a precancerous lesion and that detection of this abnormality in cervical cytology specimens may differentiate between lesions that will progress versus regress. There is also some preliminary evidence supporting a similar role for gain of 5p and 20q in cervical cancer progression.

The present invention can provide improved screening programs for HPV-associated cancers, particularly through the identification of biomarkers associated with HPV-associated cancer progression. In specific embodiments, as described herein, the present invention provides for the use of FISH-based assays in the evaluation of biomarker indicative of HPV-associated cancer in cervical and anal cytology specimens, such as the gain of 3q, 5p, and 20q. The invention also can provide for determining whether detected genetic alterations are biomarkers of HPV-associated cancers that can successfully stratify patients into those that require additional treatment versus those who do not. In particular embodiments, this can be accomplished through use of a robust, sensitive, and specific FISH-based HPV-associated cancer detection test (FHACT) that can significantly contribute to clinical decision making in patients with abnormal cytology diagnoses, impacting clinical management and cost of care. The present invention also can allow for evaluating the commonality of genetic alterations in HPV-associated cancers and obtaining valuable information on possible common roles of these abnormalities in the etiology of the diseases.

In certain embodiments, the present invention can provide a probe set or panel of probes for detecting biomarkers in a sample indicative of HPV-associated precancer or cancer. Particularly, the probe set comprises a plurality of labeled, distinct genomic regions, wherein each of the distinct genomic regions can be individually capable of hybridizing to material present in a sample. Specifically, the genomic regions in the probe set can be regions wherein an alteration therein is correlated to one or more types of HPV-associated cancer. The probe set can be used in a FISH-based testing algorithm to identify biomarkers indicative of HPV-associated cancer and thus provide a tool for diagnosis and prognosis of HPV-associated cancers in various stages of the cancer cycle (e.g., precancer, early stage cancer, and late stage cancer).

The invention also provides methods of utilizing the probes for identifying biomarkers indicative of HPV-associated cancer. Various materials can be used in carrying out the methods of the invention, and the following discussion provides only certain embodiments encompassed by the invention. Further embodiments also are intended to be encompassed by the invention.

As noted herein, the present invention can related to specific probes useful in identifying biomarkers indicative of HPV-associated cancer. Such probes can be prepared according to various methods not limited to the exemplary embodiments described herein. In certain embodiments, the methods of the invention can be carried out using one or more probe sets commercially available. In other embodiments, the inventive methods can be carried out using specially prepared probe sets according to the invention. In still further embodiments, combinations of probe sets can be used. As used herein, the term "probe set" is intended to mean a single set and/or two or more sets, wherein each set can comprise a plurality of nucleic acids of varying lengths that are homologous or complementary to genomic regions (e.g., DNA fragments).

The probes of the present invention hybridize to genomic DNA, particularly a target genomic region as disclosed herein. It is recognized that for two single-stranded DNAs to hybridize to each, such as for example, a probe and a target genomic region as disclosed herein, one single stranded DNA must be complementary to the other DNA single stranded DNA. Thus, the probes of the present invention encompass nucleic acids that are complementary to either strand of the double-stranded DNA of the target genomic regions as disclosed herein. While the probes of the present invention can be fully complementary to all or at least a portion of a target genomic region of the present invention, the present invention encompasses probes that are not fully complementary to a target genomic region but that can specifically hybridize to the target genomic region under hybridization conditions disclosed herein or otherwise known one of skill in the art.

In specific embodiments, probes useful according to the invention can be prepared as described below. The following description specifically can relate to 3q, 5p, 20q, and cen7 probes, but the invention also encompasses similar modes of preparing further probes that can be useful according to the invention. The following description may refer to the plurality of probe sets as a probe "cocktail", but such term is not intended to be limiting in scope and rather is used to simply reference the group of probes that can comprise one or more probe sets. In specific embodiments, 1 µg of each probe DNA mixture can be labeled by nick translation by conventional methods with the respective fluorochrome used as a label. For BAC-based probes (e.g., 3q, 5p, and 20q), labeling can be performed for 16 hours. For the plasmid-based probe (e.g., cen7), labeling can be performed for 6 hours. An aliquot can be checked by gel electrophoresis to ensure that the size of the labeled fragments is approximately 100,300 bp. A small equivalent aliquot of each labeling reaction then can be mixed and ethanol precipitated in the presence of Cot-1 DNA and human placental DNA. Following re-suspension in a hybridization mix (e.g., 60% formamide, 10% dextran sulfate, 0.2% SDS, 2×SSC), the probe cocktail can be hybridized to a control slide (as further described herein) and scored manually to confirm adequate labeling of each probe. If all differentially-labeled probes are well visualized and of roughly equal intensity, the remainders of each labeling reaction can be mixed in equivalent amounts. If unequal signals are observed for the probes, then upon mixing of the four probes, appropriate adjustments can be made to the volume of each added. In either case, Cot-1 DNA and human placental DNA can be added prior to ethanol precipitation with 0.3M NaOAc. The formed pellet can be re-suspended in 50 µl hybridization mix. On average, 1 µg (1 µl) of each probe may be sufficient for approximately 10 hybridizations of circles covered by 18 mm² coverslips.

For each new "lot" of probe cocktail prepared, hybridization of a control slide can be performed for titration of fluorochromes as described above. In addition, for each batch of ten specimens submitted to FHACT, a control slide preferably can be hybridized to control for hybridization conditions. The control slide can comprise two areas of hybridization, one containing nuclei of normal peripheral blood lymphocytes (PBL) (negative control) and the other of the cancer cell line. For example, in relation to cervical cancer, CaSki can be used and is known to exhibit gain of 3q and 5p (positive control). The normal peripheral blood lymphocytes on the control slide typically can comprise, for example, an equimixture of PBL from three females and three males.

Various methods can be used in specimen preparation. For example, cervical cytology specimens for FHACT can be received in PreservCyt™ and SurePath™, alcohol-based preservation media used routinely for the preservation of cervical specimens in preparation for cervical thin-layer cytology. For FISH, the specimen cells preferably can be transferred into Carnoy's fixative, (3:1 methanol:acetic acid), which removes most of the cytoplasm leaving nuclei open to hybridization with the DNA probe. The Carnoy's fixative evaporates rapidly facilitating the spreading of nuclei when making air-dried slides. Thus the cells of the coded specimen (approximately 0.5-1 ml) can be pelleted (such as by centrifugation), re-suspended in fixative, and left for about 30 minutes. Alternately, the cells can be stored overnight of longer (e.g., at 4° C.). The fixative then can be changed at least two times just prior to use or for longer storage (e.g., –20° C. for up to 3 years). In specific embodiments, about 0.5-1.0 ml residual cytology specimen can be sufficient material (nuclei) for an average of about 4-20 hybridization areas having a dimension of about 18 mm².

Specimen slides can be prepared according to a variety of methods. In specific embodiments, just prior to slide preparation, the cells can be pelleted and re-suspended in approximately 30 µl of fixative depending on the size of the pellet, of which <8 µl is applied to one circle on the plus side of a two-sample coated slide. A second specimen can be applied to the other circle. The slides can be air-dried for one day prior to hybridization.

Prior to hybridization, slides can be with pepsin (e.g., 0.004% in 0.01N HCl) at for a time of about 15 minutes at a temperature of about 37° C., washed twice in PBS at room temperature (RT) for 5 minutes each, post-fixed in 1% formaldehyde for about 5 minutes at RT, dehydrated in an ethanol series (e.g., 70% and 100%) for 2 minutes each at RT, and air-dried. The FHACT probe cocktail in hybridization mix (50) then can be applied to each target area of the slide (a circle), coverslipped, and sealed (such as with rubber cement). The probe/hybridization mix and specimen can be co-denatured (e.g., at about 80° C. for 2 minutes) and incubated overnight in a humidified chamber (e.g., at about 37° C.). After removal of the rubber cement and the coverslip, the slide can be submitted to two washes in 2×SSC plus 0.1% Tween-20 (e.g., 45° C. for about 5 minutes), and rinsed briefly in distilled water at RT. The slides then can be air-dried, DAPI counterstain applied, and coverslipped. Slides preferably are kept in a light-sensitive box until scoring is performed.

For each hybridization batch, the control slide initially can be scored using any suitable equipment type, such as an epi-fluorescence microscope equipped with filters to view the red, green, blue, and gold hybridization signals arising from the labels used in this embodiment. The microscope also can include a CCD camera. An exemplary operating system is the Isis Imaging Software (available from Metasystems).

The slide first can be examined for cell density, background, nuclear morphology, and hybridization signal strength. Using established criteria (e.g., derived from experience in performing FISH with other probes on clinical specimens), the quality of hybridization can be ranked and, if suitable for analysis, is scored. In one method for scoring, 300 or more nuclei are consecutively scored where nuclei are not scored if they are: 1) overlapping such that the signals belonging to each nucleus cannot be distinguished; 2) are scratched or otherwise physically damaged; 3) are partially covered by fluorescent debris which might obscure signals; 4) have signals which are pale or irregular and cannot be distinguished from background; and 5) do not have at least one red, one green, one blue, and one gold signal (i.e., at least one signal for each label color used). For scoring, each signal must be on or touching the DAPI-stained nucleus, be larger than background spots, and be a single spot, a closely-spaced doublet (less than one signal-width between), a closely-spaced cluster, or a continuous string. The nuclei are scored according to the signal patterns obtained for each probe set, where the expected normal pattern would be two signals of each color. Once it is determined that the controls are within the established ranges, the specimen slides are scored in a manner that is essentially the same as the control slide except that 300 or more nuclei are scored. In this embodiment, the patterns of hybridization (# red signals; # green signals; # gold signals; # blue signals) and the number of cells exhibiting these patterns are recorded. The number of cells with an abnormal pattern (e.g., more than two signals of red, green, gold, and/or blue) with the respective abnormality are calculated.

In specific embodiments, it can be useful to establish a basis for preliminary cut-offs. In one embodiment, abnormal and normal specimens can be used to establish the cut-off that will provide optimal sensitivity and specificity for the separation of the two specimen types. The cut-off can be determined for each abnormality as well as for various combinations of the four. Specimens also could be called positive or negative for each abnormality as well as for various combinations of the four.

The present invention can be carried out using samples (i.e., specimens) in a variety of forms. In certain embodiments, the test sample comprises all or part of a biopsy or biopsy specimen. In other embodiments, the test sample comprises tissue that is fresh, frozen, or formalin-fixed paraffin-embedded (FFPE). In further embodiments, the test sample comprises all or part of a biospecimen, such as cytology, fresh frozen biopsies and larger excisions (LEEPs), cervical secretions and blood, to name a few. The test sample particularly comprises genetic material. Preferably, the test sample comprises material in some form capable of hybridizing to the genomic regions represented on the probes used according to the invention. In specific embodiments, the test sample comprises DNA or fragments thereof. Tests samples include, for example, any tissue or fluid sample suspected of comprising an HPV-associated cancer or precancer. In a one embodiment of the invention, the tests samples are tissue or fluid samples from the cervix or anus. In other embodiments, the tests samples are tissue or fluid samples from the vulva, vagina, penis, oropharynx, pharynx, or any other tissue that is suspected of comprising an HPV-associated cancer or precancer.

EXPERIMENTAL

Specific studies were performed in development of the inventive FISH-based HPV-associated precancer and cancer detection test (FHACT). The test is useful for detection of HPV-associated precancer and cancer.

Initially, specific regions and appropriate probes were identified for use in the FHACT test. As described above, gain of 3q, 5p, and 20q are genomic abnormalities that are common to some extent in several HPV-associated diseases. As also noted above, there is evidence that, along with HPV, such abnormalities can have an early role in carcinogenesis. At least for 3q gain, there is some indication that it may represent a biomarker for distinguishing cervical lesions that progress versus those that regress. To this end, a probe was designed that is informative for the respective region incorporating TERC, a target gene associated with the gain. The seven bacterial artificial chromosomes (BACs) comprising the 3q probe were selected using the UCSC Genome Browser of the human genome sequence NCBI Build 36.1 (http://genome.ucsc.edu), based on genomic location (3q26), on lack of noted chimerism, and on relative content of repeat sequences. The cen7 probe fluorochrome was changed due to the inclusion of additional probes (5p and 20q) and taking into consideration the differential fluorochrome intensity and the ease of enumeration of the different sized signals.

As no candidate gene/region has been identified to date for the 5p gain, a probe was designed for a region on 5p15 comprising four BACs. This probe was grown, prepared, and labeled at CGI with SpectrumGreen™ (green).

For 20q, while two minimal regions of gain have only recently been identified (20q11.2 [4.1 Mbp] and 20q13.13 [3.1 Mbp]), a single BAC (RP11-30F23) mapping to 20q13.1 was used to confirm 20q gain in premalignant lesions. The present inventors have identified a probe for 20q13.1 for use in the FHACT comprising three BACs. In this case, the probe can be labeled with EnzoGold525™ (gold).

For each probe generated to date, the size of the respective labeled product was confirmed and, if needed, optimized in an additional labeling reaction.

As in the routine development of any probe to be utilized in a clinical FISH-based assay, labeled probes are initially hybridized to normal peripheral blood lymphocyte preparations (includes both interphase and metaphase cells). This is two-fold in purpose: to confirm the expected chromosome hybridization localization, and to rule out chimerism. The three probes, hybridized as a cocktail, were found to be non-chimeric and to hybridize to the correct location on reverse-DAPI-stained metaphase chromosomes. A representative image of normal lymphocyte metaphase and interphase nuclei hybridized with the four probes, confirming lack of chimerism and correct chromosomal site, is shown in FIG. 1.

Following the initial routine work-up of probes for use in FISH-based assays, several residual cervical smear cells in PreservCyt™ with known and unknown cytology were commercially obtained. A representative FISH image of interphase nuclei in a residual cervical cytology specimen with no intraepithelial neoplasia or malignancy showing a normal diploid signal pattern for all four probes is shown in FIG. 2. It also shows those obtained for a CIN3 specimen, with an abnormal pattern of 3R, 3G, 3Go, 2B. This abnormal pattern is indicative of gain of 3q, 5p, and 20q. Thus, the 3q, 5p, 20q, and cen7 probe cocktail performs well in the specimen types to be studied with no clear evident hybridization problems.

Cut-offs were not established for the 3q, 5p, 20q, and cen7 probes since, under practical concerns, these typically need to be established using the specimen type to be used in the assay due to artifacts within the specimen type that may interfere with the scoring criteria. This would be residual cervical/anal/oropharyngeal cytology specimens in PreservCyt™ and SurePath™ media.

For all probe sets, the genomic sequences spanned by each respective probe set and expected to serve as fluorescence in-situ hybridization targets are:

3q26: chromosome 3, nucleotide 170,547,508 to nucleotide 171,451,296 (SEQ ID NO: 1);

5p15: chromosome 5, nucleotide 9,134,024 to nucleotide 9,735,238 (SEQ ID NO: 2);

20q13: chromosome 20, nucleotide 42,415,838 to nucleotide 42,908,890 (SEQ ID NO: 3); and Cen7: chromosome 7, nucleotide 61,607,721 to nucleotide 61,608,041 (SEQ ID NO: 43) (All nucleotide positions are according to the March 2006 NCBI Build 36 (hg18)).

The clones used for probe preparation and their corresponding nucleotide positions with the chromosomes 3, 5, 7 and 20 are provided in Table 4. For the cen7 probe, the fragment of human DNA contained within the plasmid is 321 bp in length and exhibits greatest homology to chr7: 61,607,721-61,608,041 (99.4%). Due to the well-known repetitive nature of sequences at and near centromeric regions including cen7, the cen7 probe of the present invention is expected to hybridize to additional regions in the vicinity of the centromere of chromosome 7 that exhibit high homology to the cen7 probe. Additional sequences in chromosome 7 that also exhibit high homology include, for example: nucleotide 61,604,830 to nucleotide 61,605,150 (97.5%); nucleotide 61,606,019 to nucleotide 61,606,339 (98.8%); nucleotide 61,607,041 to nucleotide 61,607,361 (97.5%); nucleotide 61,610,103 to nucleotide 61,610,405; nucleotide 61,612,138 to nucleotide 61,612,450 (92.4%); Due to the high homology, these sequences are expected to serve as additional hybridization targets of the cen7 probe with the entire region spanned by the sequences of high homology being chromosome 7 nucleotide 61,604,830 to nucleotide 61,612,450.

TABLE 4

Clones Used For Probe Preparation and Corresponding Nucleotide Positions on Chromosomes

| Chromosomal Segment | Clone | Chromosome | Start Nucleotide[1] | End Nucleotide |
|---|---|---|---|---|
| 3q26 (Red) | 1 | 3 | 170,547,508 | 170,734,205 |
|  | 2 | 3 | 170,655,688 | 170,810,114 |
|  | 3 | 3 | 170,776,548 | 170,968,089 |
|  | 4 | 3 | 170,830,768 | 170,980,869 |
|  | 5 | 3 | 170,975,610 | 171,133,930 |
|  | 6 | 3 | 170,099,036 | 171,303,928 |
|  | 7 | 3 | 171,272,078 | 171,451,296 |
| 5p15 (Green) | 1 | 5 | 9,134,024 | 9,322,468 |
|  | 2 | 5 | 9,273,776 | 9,469,235 |
|  | 3 | 5 | 9,404,142 | 9,596,539 |
|  | 4 | 5 | 9,579,237 | 9,735,238 |
| 20q13 (Gold) | 1 | 20 | 42,415,838 | 42,605,120 |
|  | 2 | 20 | 42,578,015 | 42,755,125 |
|  | 3 | 20 | 42,735,160 | 42,908,890 |
| cen7 (Blue) | 1 | 7 | 61,607,721 | 61,608,041 |

[1]All nucleotide positions are according to the March 2006 NCBI Build 36 (hg18).

A number of journal articles are cited herein to provide references for various disclosures. It is understood that all cited articles are intended to be incorporated herein by reference in their entirety.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09157129B2). An electronic copy of the "Sequence Listing" will also be available from the USPTO upon request and payment of the fee set forth in 37 CFR 1.19(b)(3).

That which is claimed:

1. A method of identifying an individual with one or more human chromosomal abnormalities diagnostic or indicative of one or more types of human papillomavirus (HPV)-associated cancer, the method comprising:
   (a) hybridizing a probe set with genetic material from a sample that is obtained from an individual, wherein the sample comprises genetic material from cervical tissue and/or fluid thereof, wherein hybridizing comprises fluorescence in situ hybridization (FISH), and wherein the probe set consists of
      (i) a first probe that hybridizes selectively to 3q26, wherein the first probe comprises a probe preparation of seven different nick-translated clones corresponding to chromosome 3, clones 1-7 of Table 4,
      (ii) a second probe that hybridizes selectively to 5p15, wherein the second probe comprises a probe preparation of five different nick-translated clones corresponding to chromosome 5, clones 1-5 of Table 4,
      (iii) a third probe that hybridizes selectively to 20q13, wherein the third probe comprises a probe preparation of three different nick-translated clones corresponding to chromosome 20, clones 1-3 of Table 4, and
      (iv) a fourth probe that hybridizes selectively to cen7, wherein the fourth probe comprises a probe preparation of a nick-translated clone corresponding to chromosome 7, clone 1 of Table 4; and
   (b) analyzing the hybridization pattern of the probe set to the genetic material to determine the presence or absence in the sample of a gain of 3q, a gain of 5p, a gain of 20q, and a gain of cen7, wherein a gain of 3q, a gain of 5p, a gain of 20q, and a gain of cen7 identify the individual as having one or more human chromosomal abnormalities diagnostic or indicative of one or more types of HPV-associated cancer;
   wherein the individual identified as having one or more human chromosomal abnormalities diagnostic or indicative of one or more types of HPV-associated cancer is subsequently managed and treated for HPV-associated cervical cancer.

2. The method of claim 1, wherein the genetic material comprises chromosomes.

3. The method of claim 1, wherein the identified individual is in a precancerous stage of an HPV-associated cancer.

4. The method of claim 1, wherein the probe that hybridizes to 3q26 is capable of hybridizing to SEQ ID NO: 1 or complement thereof.

5. The method of claim 1, wherein the probe that hybridizes to 5p15 is capable of hybridizing to SEQ ID NO: 2 or complement thereof.

6. The method of claim 1, wherein the probe that hybridizes to 20q13 is capable of hybridizing to SEQ ID NO: 3 or complement thereof.

7. The method of claim 1, wherein the probe that hybridizes to cen7 is capable of hybridizing to SEQ ID NO: 4 or complement thereof.

8. The method of claim 1, wherein each of the probes is labeled with a different color fluorochrome.

9. A method of identifying in a sample one or more human chromosomal abnormalities diagnostic or indicative of one or more types of HPV-associated cancer, the method comprising:
   (a) hybridizing a probe set with genetic material from the sample, wherein the sample is obtained from an individual and comprises genetic material from anal tissue and/or fluid thereof, wherein hybridizing comprises fluorescence in situ hybridization (FISH), and wherein the probe set consists of
      (i) a first probe that hybridizes selectively to 3q26, wherein the first probe comprises a probe preparation of seven different nick-translated clones corresponding to chromosome 3, clones 1-7 of Table 4,
      (ii) a second probe that hybridizes selectively to 5p15, wherein the second probe comprises a probe preparation of five different nick-translated clones corresponding to chromosome 5, clones 1-5 of Table 4,
      (iii) a third probe that hybridizes selectively to 20q13, wherein the third probe comprises a probe preparation of three different nick-translated clones corresponding to chromosome 20, clones 1-3 of Table 4, and
      (iv) a fourth probe that hybridizes selectively to cen7, wherein the fourth probe comprises a probe preparation of a nick-translated clone corresponding to chromosome 7, clone 1 of Table 4; and
   (c) analyzing the hybridization pattern of the probe set to the genetic material to determine the presence or absence in the sample of a gain of 3q, a gain of 5p, a gain of 20q, and a gain of cen7, wherein a gain of 3q, a gain of 5p, a gain of 20q, and a gain of cen7 identify the individual as having one or more human chromosomal abnormalities diagnostic or indicative of one or more types of HPV-associated cancer;
   wherein the individual identified as having one or more human chromosomal abnormalities diagnostic or indicative of one or more types of HPV-associated cancer is subsequently managed and treated for HPV-associated anal cancer.

10. The method of claim 9, wherein the genetic material comprises chromosomes.

11. The method of claim 9, wherein the probe that hybridizes to 3q26 is capable of hybridizing to SEQ ID NO: 1 or complement thereof.

12. The method of claim 9, wherein the probe that hybridizes to 5p15 is capable of hybridizing to SEQ ID NO: 2 or complement thereof.

13. The method of claim 9, wherein the probe that hybridizes to 20q13 is capable of hybridizing to SEQ ID NO: 3 or complement thereof.

14. The method of claim 9, wherein the probe that hybridizes to cen7 is capable of hybridizing to SEQ ID NO: 4 or complement thereof.

15. The method of claim 9, wherein each of the probes is labeled with a different color fluorochrome.

16. A method of identifying in a sample one or more human chromosomal abnormalities, the method comprising:
   (a) hybridizing a probe set with genetic material from the sample, wherein the sample is obtained from an individual and comprises genetic material from human tissue and/or fluid thereof, wherein hybridizing comprises fluorescence in situ hybridization (FISH), and wherein the probe set consists of
      (i) a first probe that hybridizes selectively to 3q26, wherein the first probe comprises a probe preparation of seven different nick-translated clones corresponding to chromosome 3, clones 1-7 of Table 4,
      (ii) a second probe that hybridizes selectively to 5p15, wherein the second probe comprises a probe preparation of five different nick-translated clones corresponding to chromosome 5, clones 1-5 of Table 4,
      (iii) a third probe that hybridizes selectively to 20q13, wherein the third probe comprises a probe preparation of three different nick-translated clones corresponding to chromosome 20, clones 1-3 of Table 4, and
      (iv) a fourth probe that hybridizes selectively to cen7, wherein the fourth probe comprises a probe preparation of a nick-translated clone corresponding to chromosome 7, clone 1 of Table 4; and
   (c) analyzing the hybridization pattern of the probe set to the genetic material to determine the presence or absence in the sample of a gain of 3q, a gain of 5p, a gain of 20q, and a gain of cen7, wherein a gain of 3q, a gain of 5p, a gain of 20q, and a gain of cen7 identify the individual as having one or more human chromosomal abnormalities diagnostic or indicative of one or more types of HPV-associated cancer;
   wherein the individual identified as having one or more human chromosomal abnormalities diagnostic or indicative of one or more types of HPV-associated cancer is subsequently managed and treated for the HPV-associated cancer.

17. The method of claim 10, wherein the human tissue is selected from the group consisting of cervical tissue, anal tissue, oropharyngeal tissue, pharyngeal tissue, vulva tissue, vaginal tissue; and penile tissue.

18. The method of claim 16, wherein the probe that hybridizes to 3q26 is capable of hybridizing to SEQ ID NO: 1 or complement thereof.

19. The method of claim 16, wherein the probe that hybridizes to 5p15 is capable of hybridizing to SEQ ID NO: 2 or complement thereof.

20. The method of claim 16, wherein the probe that hybridizes to 20q13 is capable of hybridizing to SEQ ID NO: 3 or complement thereof.

21. The method of claim 16, wherein the probe that hybridizes to cen7 is capable of hybridizing to SEQ ID NO: 4 or complement thereof.

\* \* \* \* \*